United States Patent
Hölzl et al.

(10) Patent No.: US 10,592,621 B2
(45) Date of Patent: Mar. 17, 2020

(54) METHOD FOR DETERMINING A STRENGTH OF A TUBE BUNDLE HEAT EXCHANGER, AND PRODUCTION METHOD

(71) Applicant: LINDE AKTIENGESELLSCHAFT, Munich (DE)

(72) Inventors: Reinhold Hölzl, Geretsried (DE); Jürgen Spreeman, Rosenheim (DE); Adriana Stefanescu, München (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 421 days.

(21) Appl. No.: 15/654,934

(22) Filed: Jul. 20, 2017

(65) Prior Publication Data
US 2018/0046739 A1 Feb. 15, 2018

(30) Foreign Application Priority Data
Aug. 9, 2016 (EP) .................................. 16001769

(51) Int. Cl.
| | | |
|---|---|---|
| G06G 7/48 | (2006.01) | |
| G06F 17/50 | (2006.01) | |
| B21D 53/06 | (2006.01) | |
| B21D 11/06 | (2006.01) | |
| G01M 5/00 | (2006.01) | |
| F28D 7/02 | (2006.01) | |
| F28F 1/00 | (2006.01) | |

(52) U.S. Cl.
CPC .......... *G06F 17/5009* (2013.01); *B21D 11/06* (2013.01); *B21D 53/06* (2013.01); *F28D 7/024* (2013.01); *F28F 1/00* (2013.01); *G01M 5/0058* (2013.01); *F28F 2200/00* (2013.01); *G01N 2203/00* (2013.01)

(58) Field of Classification Search
CPC .................................................. G06F 17/5009
USPC .......................................................... 703/7
See application file for complete search history.

(56) References Cited

U.S. PATENT DOCUMENTS

| | | |
|---|---|---|
| 3,353,250 A | 11/1967 | Wahei et al. |
| 4,984,360 A | 1/1991 | Sather et al. |

*Primary Examiner* — Hugh M Jones
(74) *Attorney, Agent, or Firm* — Millen White Zelano & Branigan, PC

(57) ABSTRACT

A method for determining a stiffness of a tube bundle heat exchanger. The heat exchanger has a core tube and a plurality of coil tubes coiled around the core tube to form a tube bundle having a plurality of coil layers at a respective layer coiling angle. The method determines a geometric strength parameter for a coil layer, the strength parameter being an area ratio of a coil-tube cross-sectional area to a cell cross-sectional area resulting from the axial spacing of the coil tubes and an outer diameter of the coil tubes. The area ratio is corrected by a correction factor taking the orientation of the coil tubes of the coil layer in relation to the force of gravity acting on the coil tubes into consideration. The stiffness of the respective coil layer is determined from the corrected area ratio and a modulus of elasticity of the coil-tube material.

15 Claims, 3 Drawing Sheets

METHOD FOR DETERMINING A STRENGTH OF A TUBE BUNDLE HEAT EXCHANGER, AND PRODUCTION METHOD

The present invention relates to a method for determining a stiffness or strength of a tube bundle heat exchanger, and a method for determining a state, such as for example a strength or a lifetime of a tube bundle heat exchanger, and a method for producing said heat exchanger.

In tube bundle heat exchangers, a plurality of thin tubes are helically coiled in multiple layers around a core tube. Tube bundle heat exchangers are also referred to as helically coiled heat exchangers. They are usually used for treating fluids, such as liquids, and have to withstand large temperature and pressure fluctuations.

During production, transport and operation, corresponding tube bundle heat exchangers, or the materials used therein, are subject in particular to mechanical and thermal influences. For example, the material properties and thicknesses have to be adapted to respective application and requirement situations. In particular, the weight of the multiple coiled tubes on the respective core tube and/or on the respective coil layer positioned below plays a role here.

It has been found that, during the production of corresponding tube bundle heat exchangers, the inner mechanical stresses cannot be neglected. In known production methods, the core tube and the semi-coiled coil tubes rotate about a bundle axis. The system, comprised of the core tube and the coil tubes to be coiled therearound, is in this case subject to mechanical loading between the bearing points. Here, it is desirable to be able to estimate the changing strength of the resulting tube bundle heat exchangers. In the past, the strengths or stiffnesses of such systems were calculated by way of simple models, with rods or equivalent cylinders taken into consideration.

It is furthermore desirable to predict the mechanical and thermal stresses of corresponding tube bundle heat exchangers during operation, in order to estimate the lifetime, susceptibility to maintenance or stability thereof. For this purpose, there is a need for simulation methods which, in addition to the mechanical stresses, also take into consideration thermodynamic influences. In all these simulations, the reliable determination of the stiffness of the tube bundle system is especially desired.

It is therefore an object of the present invention to provide improved possibilities for simulation modelling and determination in order to gain an understanding of the tube bundle heat exchanger.

Said object is achieved by a method as described herein.

A method for determining a stiffness of a tube bundle heat exchanger is accordingly proposed. The tube bundle heat exchanger considered comprises a core tube and coil tubes coiled around the core tube to form a tube bundle, wherein the coil tubes are coiled in a plurality of coil layers and at a respective layer coiling angle around the core tube. The following steps are performed:

determining a geometric strength parameter of a respective coil layer, wherein the geometric strength parameter comprises an area ratio of a coil-tube cross-sectional area to a cell cross-sectional area, wherein the cell cross-sectional area results from the axial spacing of the coil tubes and an outer diameter of the coil tubes;

correcting the area ratio by a correction factor for the purpose of taking into consideration the orientation of the coil tubes of the respective coil layer in relation to the force of gravity acting on the coil tubes; and determining the stiffness of the respective coil layer in dependence on the corrected area ratio and a modulus of elasticity of the coil-tube material.

In the proposed method, the orientation of the coil tubes in relation to the force of gravity is taken into consideration by way of a correction factor. In certain production situations for tube bundle heat exchangers, the core tube extends horizontally along an axial direction of the bundle. The coil tubes contribute, in particular in layers, to a strength of the tube bundle heat exchanger. In the case of modellings assumed for the sake of simplicity in the past, the coil layers were considered as simple circular cylinders, however, whereby the influence of helical coiling of the coil tubes was disregarded. It is now proposed to establish the correction factor in dependence on the layer coiling angle. As a result, an improved estimate or determination of the stiffness is achieved.

In certain operating situations, the axial direction of the bundle extends vertically, so that the force of gravity acts vectorially along the core tube. In this configuration too, the influence of the force of gravity on the stiffness is taken into consideration with the aid of the correction factor.

In embodiments, the correction factor is selected to be proportional to a sine of the layer coiling angle. In particular in the case of horizontal mounting of the core tube or a horizontal arrangement of the bundle axis, a correction factor which is defined as the sine of the layer coiling angle results in a projection of the portion of the coil tubes that has an influence on the stiffness onto the acceleration due to gravity. In this respect, the correction factor ensures that the vectorial component of the force of gravity on the inclined coil is taken into consideration. The stiffness is in particular a flexural stiffness, which depends on the modulus of elasticity of the respective coil-tube material. Examples of suitable materials are aluminium and stainless steel. However, other materials are also conceivable.

In this respect, the method comprises one step: calculate a flexural stiffness of a coil layer of a tube bundle by using a strength model of an equivalent tube made of a coil-tube material, wherein the equivalent tube corresponds to a coil layer, and the equivalent tube is weighted with an area ratio of the coil-tube cross-sectional area to the cell cross-sectional area, wherein a correction factor which depends on a coiling angle reduces the flexural stiffness.

In embodiments, for determining the stiffness of the respective coil layer, the coil layer is modelled as a circular cylinder produced from the coil-tube material. Furthermore, the determination of the area ratio and of the correction factor results in realistic modelling being achieved. That is to say, it is possible, in particular during the production of a tube bundle heat exchanger, for the support and rotation situation to be set up in such a way that no excessive stresses on the materials arise and the heat exchanger can be reliably produced.

In embodiments, the method further comprises determining a stiffness of the tube bundle in an axial direction of the bundle. Here, the flexural stiffness is determined, by means of which the resulting curvature along the axial direction of the bundle can be estimated. In turn, a stress analysis can be derived.

In embodiments, the method comprises at least one of the steps of:

determining a stiffness of the core tube; and determining a stress acting on the core tube in dependence on a mass of the coiled coil tubes of the coil layers and on the determined stiffness of the coil layers.

It can be said that a stress analysis for the tube bundle heat exchanger system, comprised of core tube and coil layers, can be realized, wherein the load on the bundle is reliably taken into consideration. In embodiments, a stress analysis of the tube bundle is performed with the aid of a finite element method. The core tube, the tube bundle and/or the tube bundle heat exchanger are in this case arranged horizontally on two bearing points.

Finite element methods allow structural mechanics calculations of states of mechanical systems. it is conceivable, for example, to use commercial software packages to perform stress analyses on the basis of the proposed methods for determining and estimating the stiffness.

In embodiments, the coil layers are spaced apart from one another radially with the aid of coil webs. Such coil webs for spacing apart the coil layers can likewise be taken into consideration with regard to their contribution to the strength of the tube bundle.

In embodiments, the coil tubes are spaced apart from one another in the direction of a core-tube axis or an axial direction of the bundle by a coil-tube centre-point spacing. In the case of regular coil-tube centre-point spacing, reference can also be made to a pitch which determines the extent of a periodic cell in the axial direction.

A respective coil tube can further have an inner diameter and an outer diameter. The coil-tube cross-sectional area is then determined as $¼ \times \pi \times$ the difference of the squares of the inner and the outer diameter.

In the method, in particular a corrected stiffness of the tube bundle heat exchanger is determined by selecting an averaged correction factor for determining the stiffnesses of all coil layers. For example, the coiling angle can be assumed to be the same for all layers fir the purpose of simplifying a subsequent calculation or analysis. Alternatively or additionally a correction factor can also be taken as a trigonometric function of the coiling angle for all layers of the tube bundle heat exchanger.

A circumferential line of the respective coiling surface for a coil tube and the respective coiling direction include the coiling angle $\alpha$.

In embodiments of the method for determining a stiffness, a determined stiffness of the respective coil layer is reduced by the correction factor in comparison with an equivalent stiffness which is obtained with the aid of the area ratio and a stiffness model which considers a circular cylinder. That is to say, consideration of the influence of the force of gravity or consideration only of the portion of the coil tubes contributing to the stiffness in relation to the axial direction of the bundle and/or to the force of gravity allows more realistic estimation or calculation. Compared to simple models, which take no correction factors whatsoever into consideration, the invention delivers more realistic, lower stiffnesses such that more realistic modelling or simulation takes place during the production of tube bundle heat exchangers, during transport or in the case of certain operating states.

A method for determining a state of a tube bundle heat exchanger for the purpose of a lifetime analysis is also proposed. The tube bundle heat exchanger has a core tube and coil tubes coiled around the core tube to form a tube bundle, wherein the coil tubes are coiled in a plurality of coil layers and at a respective layer coiling angle around the core tube. The stiffness of the tube bundle heat exchanger is determined with the aid of a method described above or below.

Optionally, it is in this case also possible for a variable, such as a specific heat capacity, a heat conductivity or a coefficient of thermal expansion of a respective coil layer to be determined, with the correction factor taken into consideration. In particular when estimating the correction factor by way of the sine of the coiling angle, the result is a projection of the influence of the coil tubes onto the respective variable along the bundle axis. Consequently, thermo-mechanical analyses can also be carried out more accurately and reliably.

In a method for producing a tube bundle heat exchanger, coil tubes are coiled in a plurality of coil layers and at a respective layer coiling angle around a core tube. Here, during the coiling, a stiffness of the tube bundle heat exchanger is monitored with the aid of a method presented above or below.

In the proposed methods, the layer coiling angle is in particular non-zero and between 1° and 50°, preferably between 3° and 10°. The number of coil layers is, for example, between 2 and 200. The outer diameter of the coil tubes is, for example, between 5 and 200 mm. Moduli of elasticity of the coil-tube material can be between 70,000 and 210,000 N/mm$^2$.

Furthermore, a computer program product which initiates the execution of the method or methods as described above on a program-controlled device is proposed. The execution is conceivable, for example, with the aid of a computer or a control-room computer for a process plant.

A computer program product, such as for example a computer program means, can be provided or supplied, for example, as a storage medium, such as for example a memory card, USB stick, CD-ROM, DVD, or even in the form of a downloadable file from a server in a network. This can take place, for example, in a wireless communication network by the transfer of a corresponding file with the computer program product or the computer program means.

The method or the methods are in particular software-implemented, and below reference will also be made synonymously to a simulation software.

Further possible implementations of the invention also comprise combinations of features or embodiments described above or below with regard to the exemplary embodiments that have not been specified explicitly. The person skilled in the art will also add individual aspects as improvements or supplementations to the respective basic form of the invention.

Further advantageous configurations and aspects of the invention form the subject matter of the exemplary embodiments of the invention described below, The invention is explained in detail hereinafter on the basis of preferred embodiments with reference to the appended figures.

FIG. 1 diagrammatically shows an embodiment of a tube bundle heat exchanger in partial cross section.

FIG. 2 shows a diagrammatic illustration of a coiling surface for the purpose of explaining a layer coiling angle.

FIG. 3 diagrammatically shows an embodiment of a tube bundle heat exchanger in cross section with respect to the longitudinal axis.

Figure 7:
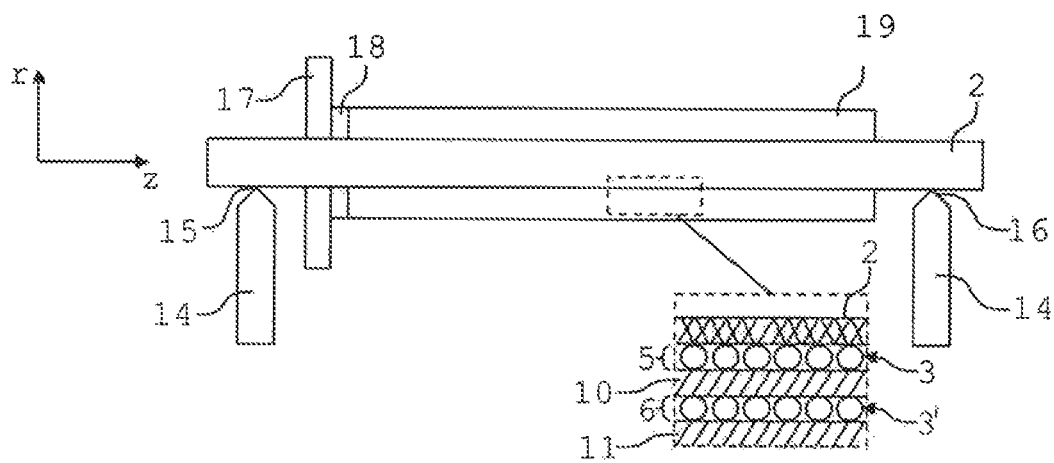
Figure 8:
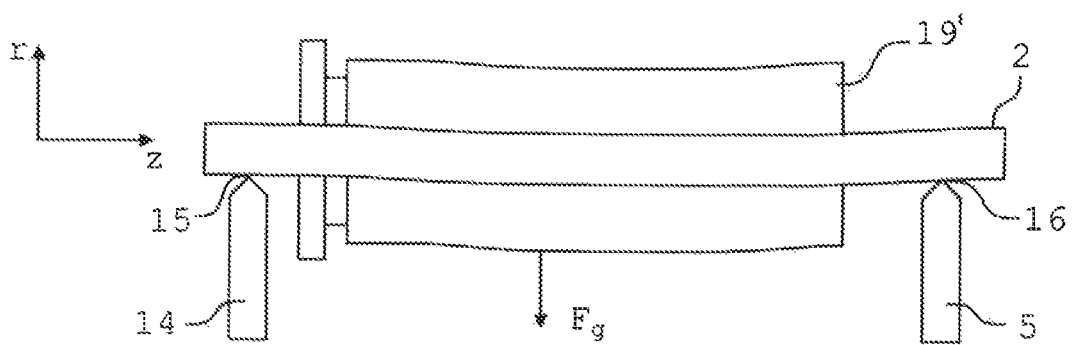

FIG. 7 and FIG. 8 shown horizontally mounted tube bundle heat exchangers for the purpose of explaining a production method thereof In the figures, elements that are identical or have the same function are provided with the same reference signs, unless stated otherwise.

Figure 1:
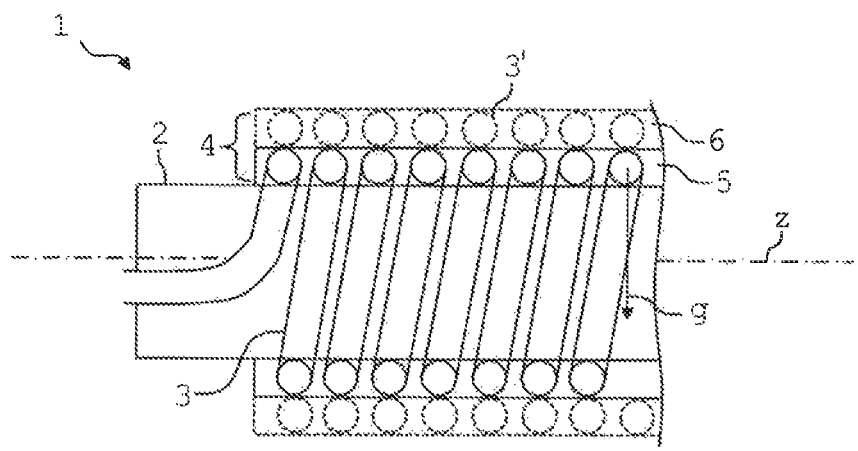

FIG. 1 shows a first exemplary embodiment of a tube bundle heat exchanger 1. Tube bundle heat exchangers or helically coiled heat exchangers comprise tube bundles coiled in a plurality of layers onto a core tube. Reference is also made to helically coiled heat exchangers in which coil tubes are coiled on about a longitudinal or bundle axis z. In FIG. 1, an axial direction z of the bundle, about which a core tube 2 extends, is given. Coil tubes 3 are helically coiled around onto the core tube 2. In the illustration of FIG. 1, a section of the resulting tube bundle heat exchanger 1 is indicated.

A first, inner coil layer 5 comprises helically coiled tubes 3. A further coil layer 6 having further coil tubes 3' is attached radially outwardly. It is possible for the coil tubes 3, 3' to not bear against one another directly, but to be spaced apart radially via webs. Although only two coil layers 5, 6 are indicated in FIG. 1, embodiments of tube bundle heat exchangers have up to 100 layers.

In the orientation of FIG. 1, the bundle axis z extends horizontally. In particular during the production of corresponding tube bundle heat exchangers 1, the coil tubes 3, 3' are coiled on from the inside outward. Here, the plurality of coil layers 5, 6 are created. During operation and use on site, such tube bundle heat exchangers 1 are usually set up vertically. That is to say, the heat exchangers are subject to particular mechanical loads transversely to their axial extent only during production and, for example, during transport on a lorry or goods train. This is in particular due to the forces acting on the core tube 2 and the inner coil layers 5, on account of the weight of the coil layers 6 lying on top. Corresponding tube bundle heat exchangers can have weights of 2 to 300 t with diameters of several metres. Aluminium or stainless steel variants are usually used as materials for the coil tubes.

In order that, during production and during transport, the tube bundles 4 and the core tube 2 are not damaged nor subject to excessive loading, it is desirable to determine or to estimate in advance the strength or the stiffness of the resulting system comprised of the core tube 2 and the tube bundle 4. For this purpose, simulations can be carried out. Investigations by the applicant have shown that in this case in particular the influence of the tube bundles 5, 6 on the stiffness along the bundle axis z is of importance, and in this case only the vectorial contribution in relation to the acceleration due to gravity g, which is indicated in FIG. 1, should be taken into consideration.

Figure 2:
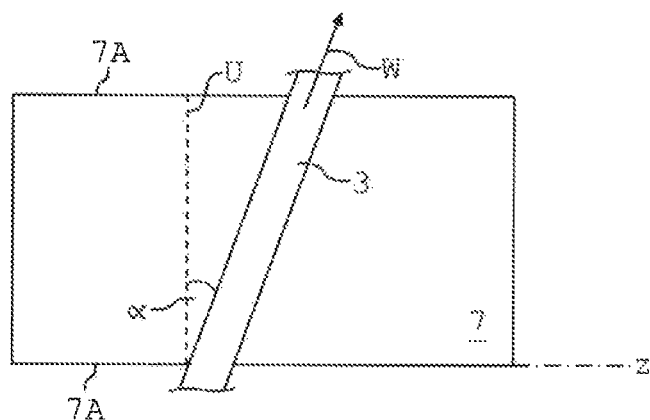

In FIG. 2, a coiling surface 7 is diagrammatically illustrated for the purpose of explaining the coiling angle α. The coiling surface 7 is the surface of an imaginary circular cylinder with a longitudinal axis z, onto which surface a corresponding tube bundle 5 (cf. FIG. 1) is coiled. A single tube 3 with a coiling direction W is indicated in FIG. 2. The dashed line U corresponds to a circumferential line of the coiling surface 7. FIG. 2 shows an unfolded lateral surface of the corresponding cylinder, that is to say the upper and lower boundaries 7A coincide on the lateral surface. The angle α, which is referred to as the coiling angle, is included by the circumferential line U and the coiling direction W.

The mechanical stability or stiffness along the axial direction z, that is to say along the bundle axis, is then not influenced by the entire material with its modulus of elasticity, but only by the projection onto the z-axis. In order in particular to determine the flexural stiffness of the entire system, it is not sufficient in this respect to consider the coil layers 5, 6, as illustrated in FIG. 1, as tubes or cylinders. Investigations by the applicant have in fact revealed that it is necessary to consider a correction factor in order to determine strength or stiffness realistically.

Figure 3:
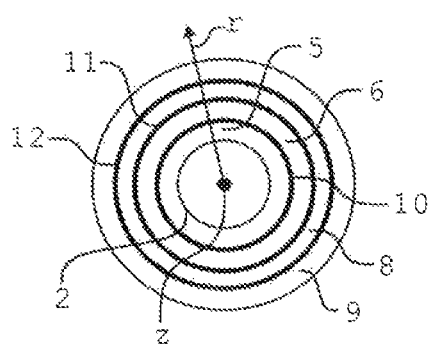

In FIG. 3, a diagrammatic cross section with respect to the longitudinal axis z of a tube bundle heat exchanger can be seen, wherein, radially from the inside outward, first the tube core 2 is present. Coiled onto this is a first coil layer 5 with coil tubes, a second coil layer 6, a third coil layer 8 and a fourth, outer coil layer 9. Webs 10 are provided for the radial spacing between the first and second coil layer. In the same way, further webs 11, 12 are provided between the second and third coil layer 6, 8 and between the third coil layer 8 and the fourth, outer coil layer 9.

In the past, the stiffnesses of the resulting tube bundle heat exchanger 1 were determined with the aid of equivalent cylinders in the form of the coil layers 5, 6, 8, 9, with a weighting of the area ratio of the coil tubes to the periodic cells. This has not always proven to be reliable, and so, to take into consideration the force of gravity acting on the coil tubes, a correction factor, in particular for determining the area ratio, is proposed.

Figure 4:
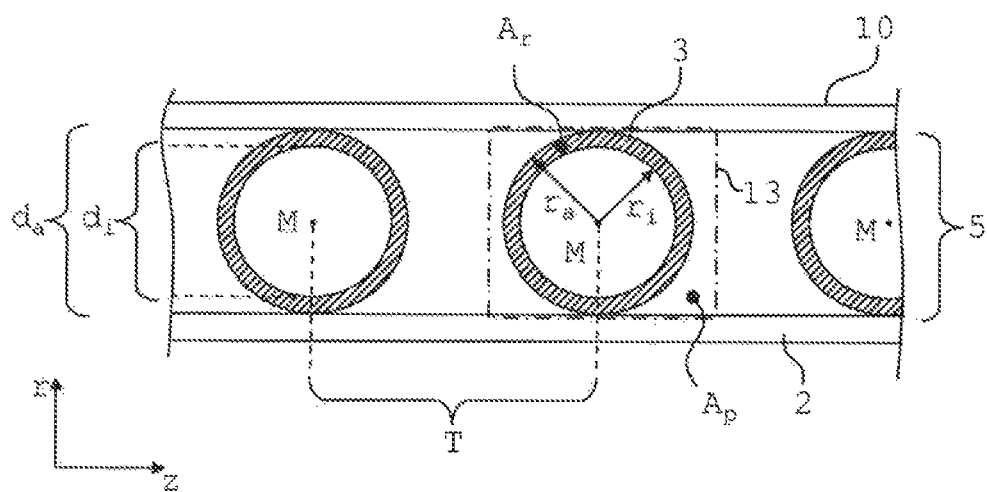
FIG. 4 shows a detailed illustration of a coil layer in cross section.

FIG. 4 shows a detailed view of a coil layer 5. Here, the figure illustrates a cross section through the coil tubes 3. In FIG. 4, the horizontal axis extends along the axial direction of the bundle z, and the radial distance r is indicated upwardly. The cross section of the core tube 2, onto which a first coil layer 5 is coiled around with coil tubes 3, is shown. The coil tubes 3 have respective centre points M and a circular cross-sectional area with in each case an inner radius $r_i$ and an outer radius $r_a$. This results in an inner diameter $d_i$ and an outer diameter $d_a$, as indicated on the left in FIG. 4. The radial extent of the coil layer 5 corresponds in this case to the outer diameter $d_a$. It can also be seen that the centre points M are, in a regular manner, at an axial spacing T from one another. It is therefore possible to define a periodic cell 13 which results from the coil-tube centre-point spacings T. The cell is indicated as a dash-dotted line by 13. A coil web 10, which can for example be modelled as a cylinder, is attached radially outwardly.

In order to estimate a strength analysis or a stiffness of the resulting tube bundle heat exchanger, the area ratio of the area $A_p$ of the unit cell 13 to the resulting coil-tube cross-sectional area $A_r$ is considered. The coil-tube cross-sectional area $A_r$ can be determined as $A_r = \frac{1}{4} \times \pi \times (d_a^2 - d_i^2)$.

The cross-sectional area of the cell $A_p$ is $A_p = T \times d_a$. The ratio $A_p/A_r$ is an important parameter for determining the stiffness of the coil layer 5. Furthermore, however, the coiling angle α (not shown in FIG. 4) is also taken into consideration. The applicant has realized that, in the modelling for the stiffness, the area ratio $A_p/A_r$ alone leads to higher values than is actually the case. Consequently, the portion of the coil tubes of a coil layer is projected onto the longitudinal axis. This results in a correction factor sin α<1, whereby a realistic result is obtained in further calculations of the stiffness or flexural stiffness. In particular during the production or during the transport of tube bundle heat exchangers, the load on the core tube under the influence of the tube bundles and of a mounted support can therefore be taken into consideration better.

The proposed area ratio $A_p/A_r$ with a correction factor sin α can be taken into consideration in further numerical stress analyses, for example with the aid of finite element methods. In addition, further material parameters, such as the modulus of elasticity of the respective coil-tube material, are included. In exemplary embodiments, the pitch or the axial extent of the cell is 18 mm, and the coil tubes have an outer diameter of 15 mm. This results in a cell cross-sectional area $A_p$=270 mm². In the case of an inner diameter of the coil tube of 14.1 mm, a tube cross-sectional area of 20.57 mm² is obtained. A coiling angle is for example 5°, and so the correction factor is sin 5°.

Figure 5:
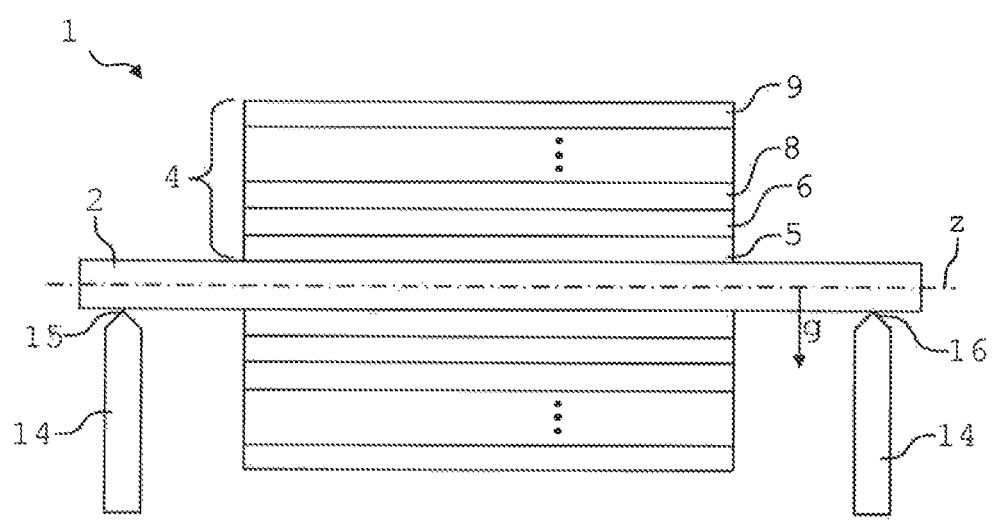
FIG. 5 shows an embodiment of a horizontally mounted tube bundle heat exchanger in longitudinal section.

FIG. 5 shows a further exemplary embodiment 5 of a tube bundle heat exchanger during production. During production, a respective coil 5, 6, 8, 9 is coiled in layers onto a core tube 2, which is supported at two bearing points 15 and 16 via supports 14. In this case, the resulting tube bundle 4 rotates about the z-axis or the bundle axis z. Here, it is possible to coil on up to 100 layers. In particular in the case of this horizontal mounting, the force of gravity g acts on the core tube 2. As already indicated above, a stiffness for the respective coil layer 5, 6, 8, 9 follows from an area ratio $A_p/A_r$ and the correction factor for taking into consideration the component of strength of the coil tubes in relation to the force of gravity g, and a modulus of elasticity of the coil-tube material. The tube material may for example have a modulus of elasticity of 190,000 N/mm². The flexural stiffness can be estimated accordingly and passed on for further processing, for example a finite element method.

Figure 6:
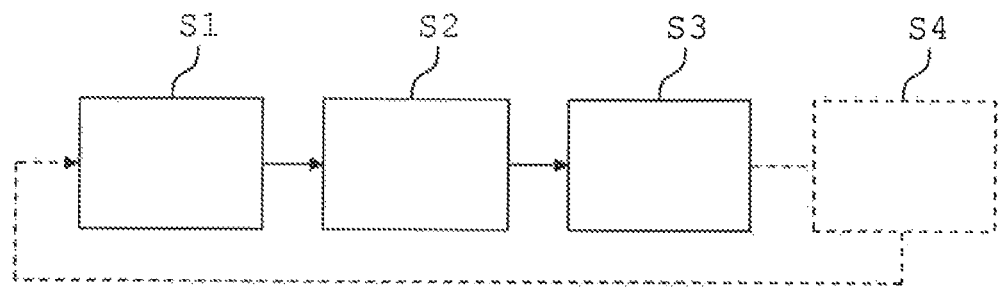
FIG. 6 shows a diagrammatic sequence of method steps for determining the stiffness of a tube bundle heat exchanger.

FIG. 6 shows by way of example a sequence of a method for determining the stiffness of a tube bundle heat exchanger, as is illustrated in the other figures. In a first method step S1, a model is created, for example a coil layer is simulated or modelled by an equivalent circular cylinder. In step S2, said basic model is improved by the respective correction factor. For this purpose, the geometric strength parameter for the respective coil layer is determined from the area ratio $A_p/A_r$ and the correction factor in dependence on the coiling angle, for example sin α. Finally, in step S3, a finite-element calculation for determining the stiffness of the entire tube bundle heat exchanger system, with the core tube and the bundle, is performed, for example with the aid of a commercial software package. The result of the stiffness calculation can be passed on to a lifetime analysis, for example in order to determine stresses in the tube bundle heat exchanger. This is indicated by the optional step S4, For example, it is possible for the stiffness to be determined continuously even while the coil tubes are being coiled on and, as a result, for production parameters, such as coiling speeds or coiling angles, to be adapted. This is indicated in FIG. 6 by the returning dashed arrow to step S4.

FIGS. 7 and 8 diagrammatically show structural mechanics calculation results on the basis of the determined stiffnesses of the coil layers. Here, FIG. 7 again shows a mounted tube bundle which is coiled onto a core tube 2. The tube bundle 19 has in this case, as indicated in the detailed view of FIG. 7, a plurality of coil layers 3, 3' which are coiled onto the core tube 2 and which are spaced apart radially by way of coil webs 10, 11. In the orientation of FIG. 7, the bundle axis z extends horizontally, and the core tube 6 is equipped with a support plate 17 and a spacer 18 for the tube bundle 19 on the core tube 2. FIG. 7 shows the orientation of the longitudinal axis z during production or during transport on two bearing points 15, 16. In the subsequent application, the axis is swung vertically such that the support plate 17 together with the spacer support and bear the tube bundle 19.

During production, particular forces then act on the core tube 2 and the tube bundle 19' itself between the bearing points 15, 16, due to the weight of the tube bundles 19. This is indicated in FIG. 8. On account of the resulting flexural stiffness of the tube bundle which is indicated by 19' in FIG. 8 and comprises further coil layers, there is a curvature or a certain sagging between the bearing points 15, 16. Due to the determination of the stiffnesses of the coil layers in the tube bundle 19, 19', it is now possible to determine the stress in the system, for example with the aid of a finite element calculation method. As revealed by investigations by the applicant, the result is a particular stressing of the mechanical system of the tube bundle heat exchanger in certain regions.

On account of the simulation and estimation or calculation of the strengths and stiffnesses, these numerical stress analyses can be carried out reliably during processing and production and also during transport. The same applies to transport, for example on a lorry, where tube bundle heat exchangers are mounted horizontally. Furthermore, with the aid of analogue correction factors which simulate a projection in the axial direction, the possibility arises for correcting further simulation parameters. It is conceivable, for example, for the heat conductivity along the bundle axis z or for coefficients of thermal expansion to be assumed in an accordingly realistic manner. As a consequence, a thermomechanical analysis of the tube bundle heat exchanger will be facilitated and more reliable.

Although the present invention has been explained in more detail using exemplary embodiments, it is modifiable in various ways. The stated dimensions and number of coils should be understood as merely given by way of example. Moreover, a further refinement of the numerical modelling can occur beyond the geometric strength parameter and the correction factor for taking into consideration the force of gravity. Further, the stiffness under the influence of the force of gravity can be determined also in the case of vertically arranged tube bundle heat exchangers, although in the illustrated exemplary embodiments a horizontal situation has mostly been assumed. In particular during the operation of the respective tube bundle heat exchanger—after its production and transport to the place of use—the core-tube axis extends vertically. Even then, the aforementioned methods with vectorial consideration of the force of gravity and of the arrangement and also of the extent of the coil tubes in relation to the acceleration due to gravity serve for reliably determining strengths and stiffnesses.

REFERENCE SIGNS USED

α Coiling angle
$A_r$ Coil-tube cross-sectional area
$A_p$ Cell cross-sectional area
$d_i$ inner diameter of a coil tube
$d_a$ Outer diameter of a coil tube
g Acceleration due to gravity
r Radial direction
T Coil-tube centre-point spacing/pitch
U Circumferential line
W Coiling direction
z Bundle axle/axial direction
1 Tube bundle heat exchanger
2 Core tube
3 Coil tube
4 Tube bundle
5, 6 Coil layer
7 Coiling surface
7A Boundary line
8, 9 Coil layer
10, 11, 12 Webs
13 Cell
14 Support
15, 16 Bearing points
17 Support plate 18 Spacer
19 Tube bundle
S1 Modelling
S2 Correction-parameter determination
S3 Finite element calculation
S4 Coiling and model adaptation

The invention claimed is:

1. Method for determining a stiffness of a tube bundle heat exchanger, which comprises a core tube and coil tubes coiled around the core tube to form a tube bundle, wherein the coil tubes are coiled in a plurality of coil layers and at a respective layer coiling angle around the core tube, comprising the steps of:
   determining a geometric strength parameter of a respective coil layer, wherein the geometric strength parameter comprises an area ratio of a coil-tube cross-sectional area to a cell cross-sectional area, wherein the cell cross-sectional area results from the axial spacing of the coil tubes and an outer diameter of the coil tubes;
   correcting the area ratio by a correction factor for the purpose of taking into consideration the orientation of the coil tubes of the respective coil layer in relation to the force of gravity acting on the coil tubes; and
   determining the stiffness of the respective coil layer in dependence on the corrected area ratio and a modulus of elasticity of the coil-tube material.

2. Method according to claim 1, wherein the correction factor is selected to be proportional to a sine of the layer coiling angle.

3. Method according to claim 1, wherein, for the purpose of determining the stiffness of the respective coil layer, the coil layer is modelled as a circular cylinder produced from the coil-tube material.

4. Method according to claim 1, further comprising:
   determining a stiffness of the tube bundle in an axial direction of the bundle.

5. Method according to claim 1, further comprising:
   determining a stiffness of the core tube; and
   determining a stress acting on the core tube in dependence on a mass of the coiled coil tubes of the coil layers and on the determined stiffness of the coil layers.

6. Method according to claim 1, further comprising: performing a stress analysis of the tube bundle with the aid of a finite element method, wherein the core tube, the tube bundle and/or the tube bundle heat exchanger is arranged horizontally on two bearing points.

7. Method according to claim 1, wherein the coil layers are spaced apart from one another radially with the aid of coil webs.

8. Method according to claim 1, wherein the coil tubes are spaced apart from one another in the direction of a core-tube axis by a coil-tube centre-point spacing.

9. Method according to claim 1, wherein a respective coil tube has an inner diameter $d_i$ and an outer diameter $d_a$, and the coil-tube cross-sectional area $A_r$ is determined as:

$$A_r = 0.25 \times (d_a^2 - d_i^2) \times \pi.$$

10. Method according to claim 1, wherein a corrected stiffness of the tube bundle heat exchanger is determined by selecting an averaged correction factor for determining the stiffnesses of all coil layers.

11. Method according to claim 1, wherein a circumferential line of the respective coiling surface for a coil tube and the respective coiling direction include the coiling angle.

12. Method according to claim 1, wherein a determined stiffness of the respective coil layer is reduced by the correction factor in comparison with an equivalent stiffness which is obtained with the aid of the area ratio and a stiffness model which considers a circular cylinder.

13. Method for determining a state of a tube bundle heat exchanger for the purpose of a lifetime analysis thereof, said heat exchanger comprising a core tube and coil tubes coiled around the core tube to form a tube bundle, wherein the coil tubes are coiled in a plurality of coil layers and at a respective layer coiling angle around the core tube, wherein a stiffness of the tube bundle heat exchanger is determined by a method comprising:
   determining a geometric strength parameter of a respective coil layer, wherein the geometric strength parameter comprises an area ratio of a coil-tube cross-sectional area to a cell cross-sectional area, wherein the cell cross-sectional area results from the axial spacing of the coil tubes and an outer diameter of the coil tubes;
   correcting the area ratio by a correction factor for the purpose of taking into consideration the orientation of the coil tubes of the respective coil layer in relation to the force of gravity acting on the coil tubes; and
   determining the stiffness of the respective coil layer in dependence on the corrected area ratio and a modulus of elasticity of the coil-tube material.

14. Method according to claim 13, wherein, further, a specific heat capacity, a heat conductivity and/or a coefficient of thermal expansion of a respective coil layer are determined, with the correction factor taken into consideration.

15. Method for producing a tube bundle heat exchanger in which coil tubes are coiled in a plurality of coil layers and at a respective layer coiling angle around a core tube, wherein, during the coiling, a stiffness of the tube bundle heat exchanger is monitored by a method comprising:
   determining a geometric strength parameter of a respective coil layer, wherein the geometric strength parameter comprises an area ratio of a coil-tube cross-sectional area to a cell cross-sectional area, wherein the cell cross-sectional area results from the axial spacing of the coil tubes and an outer diameter of the coil tubes;
   correcting the area ratio by a correction factor for the purpose of taking into consideration the orientation of the coil tubes of the respective coil layer in relation to the force of gravity acting on the coil tubes; and
   determining the stiffness of the respective coil layer in dependence on the corrected area ratio and a modulus of elasticity of the coil-tube material.

* * * * *